US 9,980,712 B2

(12) United States Patent
Seex

(10) Patent No.: US 9,980,712 B2
(45) Date of Patent: May 29, 2018

(54) DISTRACTION AND RETRACTION ASSEMBLY

(71) Applicant: Kevin Seex, Kingswood (AU)

(72) Inventor: Kevin Seex, Kingswood (AU)

(*) Notice: Subject to any disclaimer, the term of this patent is extended or adjusted under 35 U.S.C. 154(b) by 700 days.

(21) Appl. No.: 14/154,610

(22) Filed: Jan. 14, 2014

(65) Prior Publication Data
US 2014/0194697 A1 Jul. 10, 2014
US 2018/0008252 A9 Jan. 11, 2018

Related U.S. Application Data

(62) Division of application No. 11/660,466, filed as application No. PCT/AU2005/001205 on Aug. 13, 2005, now abandoned.

(30) Foreign Application Priority Data

Aug. 15, 2004 (AU) .................... 2004904580

(51) Int. Cl.
A61B 17/02 (2006.01)

(52) U.S. Cl.
CPC .......... *A61B 17/025* (2013.01); *A61B 17/02* (2013.01); *A61B 17/0206* (2013.01)

(58) Field of Classification Search
CPC .. A61B 17/0206; A61B 17/0256; A61B 17/02
USPC ......................................... 606/90, 105, 207
See application file for complete search history.

(56) References Cited

U.S. PATENT DOCUMENTS

| 5,512,038 A * | 4/1996 | O'Neal | A61B 17/0206 600/210 |
| 5,529,571 A * | 6/1996 | Daniel | A61B 17/0206 403/90 |
| 6,090,113 A * | 7/2000 | Le Couedic | A61B 17/7032 606/86 A |
| 6,716,218 B2 * | 4/2004 | Holmes | A61B 17/8866 606/105 |
| 7,582,058 B1 * | 9/2009 | Miles | A61B 5/0492 600/202 |
| 7,892,238 B2 * | 2/2011 | DiPoto | A61B 17/02 606/103 |
| 7,981,115 B2 * | 7/2011 | Justis | A61B 90/06 606/102 |
| 8,435,269 B2 * | 5/2013 | Woolley | A61B 17/0206 600/210 |
| 2003/0236529 A1 * | 12/2003 | Shluzas | A61B 17/7079 606/105 |
| 2005/0149035 A1 * | 7/2005 | Pimenta | A61B 1/32 606/86 R |
| 2005/0245928 A1 * | 11/2005 | Colleran | A61B 17/708 606/90 |
| 2006/0271050 A1 * | 11/2006 | Piza Vallespir | A61B 17/7085 606/86 A |

(Continued)

Primary Examiner — David Bates
(74) Attorney, Agent, or Firm — Galgano IP Law PLLC; Thomas M. Galgano; Jessica G. McDonald

(57) ABSTRACT

An assembly allowing retraction of soft tissue away from a reference plane; the assembly including at least one retracting element each having a distal end with a formation allowing anchorage of the at least one retracting element. The assembly also includes a proximal end of the at least one retracting element capable of movement through at least one degree of freedom relative to the anchorage.

16 Claims, 5 Drawing Sheets

(56) References Cited

U.S. PATENT DOCUMENTS

| | | | | |
|---|---|---|---|---|
| 2007/0106123 A1* | 5/2007 | Gorek | ............... | A61B 1/32 600/210 |
| 2009/0043311 A1* | 2/2009 | Koros | ............ | A61B 17/025 606/90 |
| 2009/0131755 A1* | 5/2009 | White | ............ | A61B 17/02 600/210 |
| 2015/0230785 A1* | 8/2015 | DeVere, Jr. | ......... | A61B 17/02 600/213 |

* cited by examiner

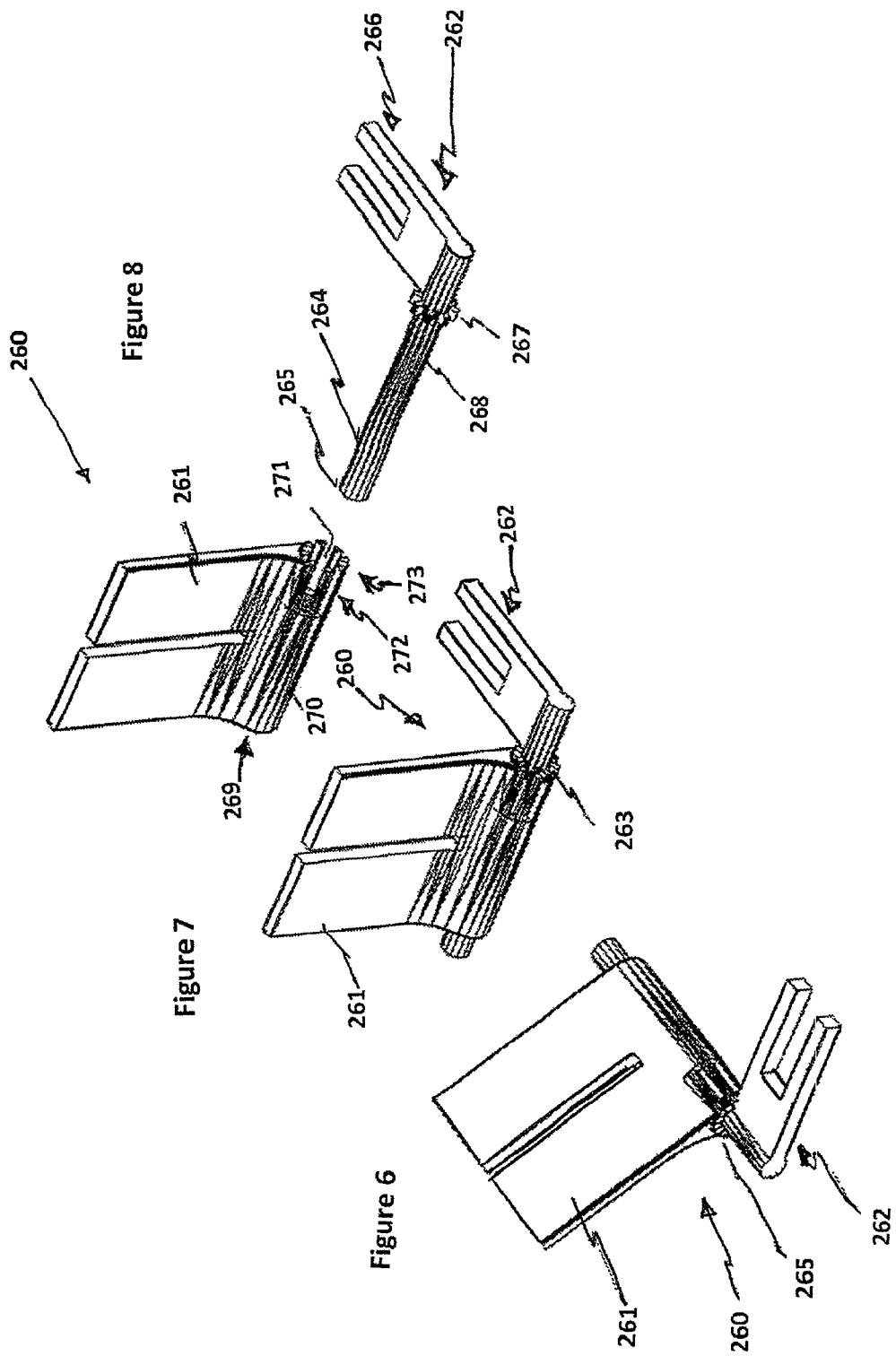

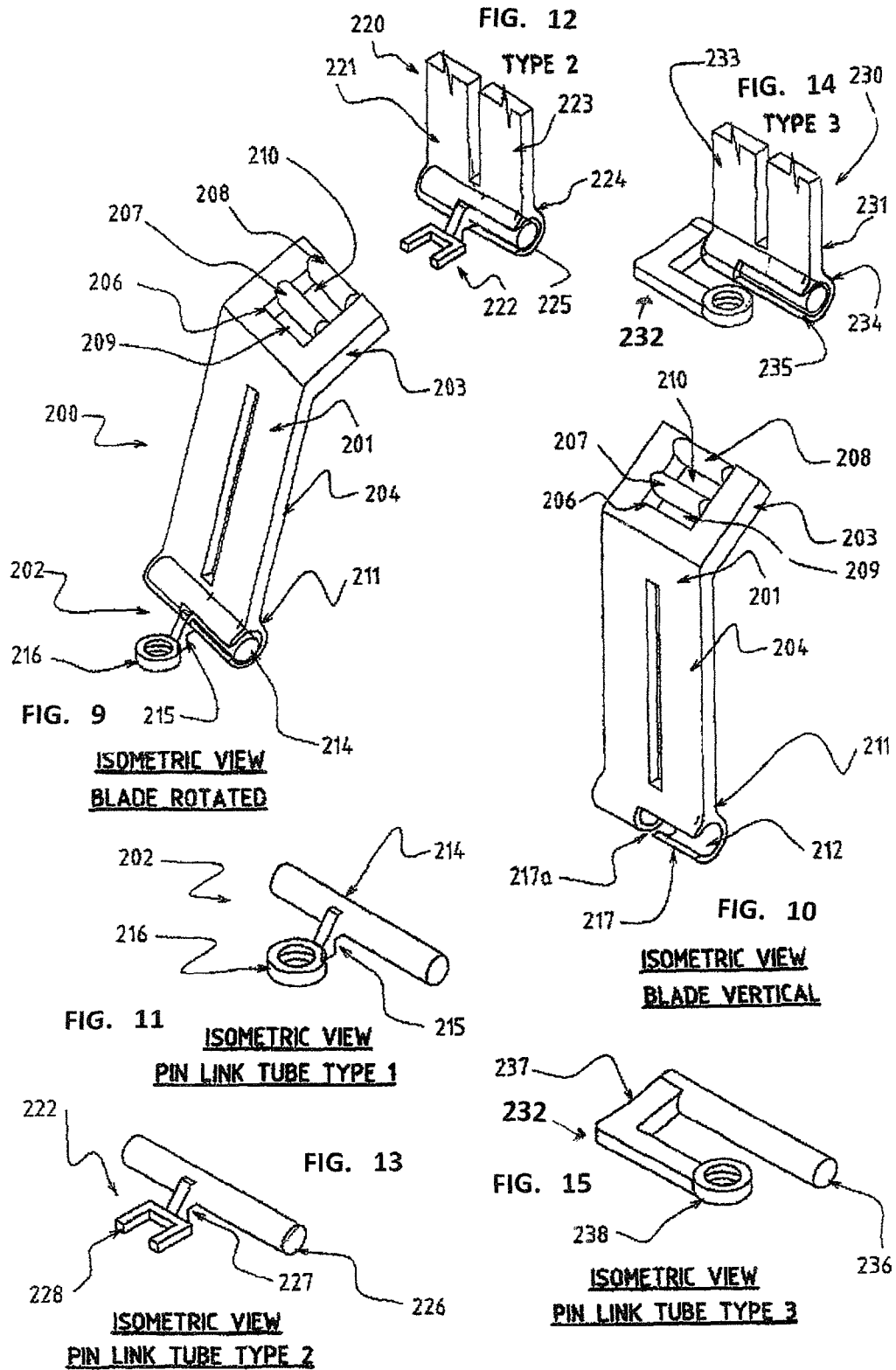

DISTRACTION AND RETRACTION ASSEMBLY

BACKGROUND

The present invention relates to distraction and retraction assemblies. The invention further relates to improved apparatuses for distraction and soft tissue retraction in surgery including, but not limited to, spinal surgery. The invention also provides an assembly which performs the function of retraction optimising mechanical advantage and efficiency in retraction and resisting unwanted pull out of retractors.

PRIOR ART

There are in existence a number of assemblies used in retraction of tissues to facilitate spinal and particularly cervical surgery. The most commonly performed anterior cervical procedure is an intervertebral fusion procedure that typically involve the steps of removing a portion or all of the affected disc material, spreading apart adjacent vertebrae with a distractor, and inserting an implant bone or cage or prosthetic disc into the space previously occupied by the removed disc material. This procedure can be done either from the front of the patient (anterior interbody fusion) or in the lumbar spine from the back (posterior interbody fusion). If done from the front, it is important to reduce the size of the retraction forces applied by the blades of the retractor so that the procedure is as minimally invasive as possible and thus minimally interferes with and minimally traumatizes the organs, tissues and vasculature being displaced to allow access to the vertebral region being treated. Posterior surgery can utilize larger tools since the insertion space is more accommodating and posterior structures requiring retraction i.e. muscles are less sensitive.

By way of an example of a known device, U.S. Pat. No. 6,017,342 discloses a compression and distraction instrument having two pivotally connected handles. Jaw portions engage objects, such as human bone, for purposes of manouvering. A control screw connects with the handles, through a mechanical advantage arrangement, and the screw pivots the jaw portions for the engagement of the objects. There is an anti-friction connection between the screw and the handles, for accurate and precise movement of the jaws. In one embodiment, the screw is axial of the instrument, and, in the other embodiment, the screw is transverse thereto, both have mechanical advantage.

In another example of a known distractor U.S. Pat. No. 6,712,825 of Mar. 30, 2004 discloses a spinal disc space distracter for separating adjacent elements, such as vertebrae. The distracter preferably has a scissors-type distracting mechanism, either in a simple scissors or double-acting scissors configuration. The distracter includes blades that are removable from the jaws of the distracter such that different blades may be used depending on the patient and situation with which the distracter is to be used. The jaws include a mating fixture and the blades include a mating portion for removable association with the mating fixture. In accordance with the principles of the invention disclosed, a spinal disc distracter is provided to allow for an implant insertion technique to be performed during distraction of the disc space. The implants are slid into the disc space between the distracter blades, preferably while the blades are in contact with the upper and lower surfaces of the adjacent vertebral bodies. The distracter is formed to be as minimally invasive and atraumatic as possible such that it may readily be used in an anterior or anterolateral approach.

There are limitations inherent in conventional self retaining retractors used widely in surgery and routinely in anterior spinal surgery. These typically have two blades typically with teeth at one end that are linked by a hinge to scissor type handles. The teeth grip into or under the tissues and apply lateral forces as the handles are compressed by the surgeon to produce the desired exposure. The teeth grip and retract both sides of a wound against each other with equal distribution of retraction force. This means that when retracting two sides with different resistances eg left and right sides of an anterior (front) cervical wound (trachea, larynx, ET tube, oesophagus and thyroid are on one side only) excessive forces and retraction are applied to the easy side in an effort to retract the opposite more resistant side. This is one reason why conventional retractors slip, twist and rise up. Placing the teeth of these retractors under the longus colli muscle (next to the spine) works to an extent and is the standard method by which retractors in the anterior (front) of the neck are secured but it is common for retractors to require repositioning several times during an operation in addition to the difficulty of securing them in the correct place initially. Teeth cannot be made too sharp or too long as they will damage vital structures The second reason they slip is because the retraction forces are coming from the top ie outside the wound at a distance to where they at required at the bottom of the wound. The path of least resistance is up and as the retractor opens even the slight bending tends to produce a vector of force up as the blade follows the path of least resistance out of the wound leading to unwanted displacement of the retractor and therefore compromised retraction. Another reason they slip is that the tissues under retraction stretch reducing their counter force. As self retaining retractors rely on counter force for stability as this is reduced loosening inevitably occurs.

Repeated adjustment can and does produce unnecessary tissue injury e.g. swallowing problems or hoarseness of voice in perhaps 5-10% of anterior cervical operations. It also wastes time and produces unnecessary bleeding. Persons skilled in the art are aware that one of the most frustrating parts of this type of surgery is positioning and maintaining position of the retractors. Conventional retractors are sometimes weighed down with chains and weights to resist the unwanted upwards rotational forces.

Some known retractor blades have short spikes for bony fixation that create a point of leverage allowing limited movement of the blade. Other retractor systems allow for fixing a retractor blade to bone within a wound via pins or screws. Some known retractor systems allow rotation of a retractor blade around an axis of rotation attached to a frame that is outside the wound e.g. Synframe™ from Synthes™.

Hohmans™ and Taylor™ retractors have an integral point that is either hammered into bone or pushed into a position to provide bone fixation and leverage. These are widely used in orthopaedic surgery. A Taylor™ type retractor blade is known which incorporates a tube for a securing pin. Also known are lever type retractors such as a hip retractor system designed by Dr R Barry Sorrells. Also know is a rail system for retractor blades and a blade that has means for fixation to bone with screws. Also known is a hip retractor system designed by a Dr S David Stulberg using only pins that are either drilled or hammered into the bone. Some of these can bend or lever slightly but allow no true rotation. External frames for securing levered retractors are also known. For example an assistant (surgeon) free self-retaining hip surgery retractor designed by Dr S David Stulberg is known.

If hammered into bone via a short point fixation, then multiple rotations produces loosening and unwanted withdrawal. Where the pins rest on their point as a simple point of leverage but without deep fixation then they are prone to slippage if knocked or an assistant surgeon is not concentrating. Accordingly, a major disadvantage of the prior art is that there are no retraction systems in use that allow free rotation without compromising fixation.

An anterior cervical system is known whereby retraction blades for cranial and caudal (top and bottom) part of wound are slid over known distraction pins. Additional lateral (side to side) retractors are still required and unconnected. These cranial and caudal blades are loose and can rotate only about the pin, (which is not very useful) and are not adjustable. They provide no lateral retraction parallel to the axis of the spine which is a much greater problem and which is addressed only in the present invention to be described below.

The Prodisc™ anterior cervical system for cervical disc replacement has distraction screws with distraction arms that slide down over screws. The Prodisc™ uses a screw cap at top that secures the distraction arm, with downward pressure on to the base of the screw.

INVENTION

The present invention in one form provides improvements in distraction and retraction assemblies. The invention further provides an improved apparatus for distraction and soft tissue retraction in surgery, including, but not limited to spinal surgery and which ameliorates the aforesaid disadvantages of the known retractors. The invention also provides an assembly which performs the functions of distraction and retraction optimising mechanical advantage and efficiency in retraction and resisting unwanted pull out of retractors. More particularly, the invention provides an assembly allowing secure anchorage of retractors and also longitudinal and rotational adjustment of the retractors to adjust retraction forces.

The invention further relates to an assembly which performs the aforesaid retraction functions in conjunction with applied distraction of vertebrae using distraction pins and co operating sleeves so that mechanical advantage in both distraction and retraction is achieved optimising efficiency in retraction and resisting unwanted pull out of retractors. Although the invention will be described with reference to its surgical applications it will be recognised by persons skilled in the art that the invention has wider applications in retraction alone and in combination retractions and distraction. During a surgical operation retractors are used to facilitate access to tissues. The present invention employs in one form the principle of fixation into bone (either directly or indirectly) to provide a secure anchorage and base for a retractor blade and also a stable axis for rotation of the blade within the wound without the prior art unwanted dislocations.

The invention improves tissue exposure and surgical site access and minimizes soft tissue injury, bruising etc (due to the more controlled and reduced movements against tissues) whilst allowing variable selective rotation of at least one retractor blade as required during the surgical procedure. The combined features of the ability to adjust retraction pressure and reduce tissue pressure applied by the retractors thus minimizing tissue injury while maintaining stability of the blade distinguishes the present invention from the known prior art. The direct or indirect fixation (anchorage) to bone of a retractor prevents unwanted slippage and avoids the need for readjustment of retractors apart from the selected amount of rotation. The stable axis of rotation from within a surgical wound also imparts a mechanical advantage to retraction pressure reducing operator fatigue. Bone fixation with rotation is achieved in a number of different ways allowing application in numerous anatomical situations.

In each of the embodiments to be described below including the direct fixation retractor assembly and the indirectly anchored retractor and distraction assemblies there exist the following common features:
1 A means for fixation to bone
2. A connection between the point of fixation and retractor (a link)
3. A means for retraction of tissues (a blade)
4. A mechanism for variable rotation of retractor blades dictated by direct or indirect fixation of the blade to bone.

The fixation to bone, link, blade and means of rotation may be direct retractor engagement or the fixation may be indirect such as that described with reference to FIG. 1 accomplished by various combinations of components.

This invention in all its forms has application whenever bone fixation is available principally in spinal and orthopaedic surgery but also other surgical disciplines. It is, another object of the present invention to provide an improved tissue retraction assembly for retracting wound margins and which provides optimal anchorage of retractor arms, optimal load application to tissue, rotational and longitudinal adjustment and which may be used in conjunction with vertebral distraction pins.

It is further an object of the present invention to provide an assembly that efficiently and simply manages the insertion of a distractor and retractor. Other objects of the present invention not explicitly stated will be set forth and will be more clearly understood in conjunction with the descriptions of the preferred embodiments disclosed hereafter.

In it s broadest form the present invention comprises an assembly for use in a surgical procedure, including a frame capable of bone distraction and which receives and retains retraction arms for retraction of soft tissue during the surgical procedure; the frame including a first member including a recess which receives a first bone anchor and a second member which co operates with the first member and receives a second bone anchor; the first member including at least one retaining arm which receives thereon a retractor arm; wherein, the second member is adjustable relative to the first member to allow distraction of bones to which the first and second bone anchors are attached.

In another broad form the present invention comprises:
an assembly for combined retraction of wound margins of soft tissue and distraction of vertebrae; the assembly including;
a pair of pins anchored in said vertebrae;
sleeves concentrically engaging said pins;
means to apply a distraction force to said pins via said sleeves;
a first side arm having a first end including a recess capable of engaging one said pins and a second end including connection means which releasably receives a first retractor arm via a mating profile;
a second side arm having a first end including a recess capable of engaging the other of said pins and a second end including connection means which releasably receives a second retractor arm via a mating profile; wherein said respective connection means each allow rotatable adjustment of each said retractor arms to retract said soft tissue margins.

In another broad form the present invention comprises:
a distraction and retraction assembly for use in a surgical procedure, the assembly including a frame capable of bone distraction and which receives and retains retraction arms for retraction of soft tissue during the surgical procedure; the frame including a first member including a recess which receives a first bone anchor and a second member which co operates with the first member and receives a second bone anchor; the first member including at least one retaining arm which receives thereon one of said retractor arms; wherein, one of said first and second members when anchored against bone is adjustable relative to the other member thereby inducing distraction of bones to which the first and second bone anchors are attached.

According to a preferred embodiment, sleeves concentrically engaging said pins; the assembly further comprising means to apply a distraction force to said pins via said sleeves.

In another broad form the present invention comprises: an assembly allowing distraction of adjacent vertebrae and retraction of soft tissue; the assembly comprising; means to apply a distraction load to said vertebrae via anchor pins fixed to each vertebrae; the assembly further including; a first side arm having a first end including a recess capable of engaging a first said pins anchored in a vertebrae, and a second end including connection means which releasably receives a first retractor arm via a mating profile; a second side arm having a first end including a recess capable of engaging a second of said pins and a second end including connection means which releasably receives a second retractor arm via a mating profile; wherein said respective connection means each allow rotatable adjustment of each said retractor arms for adjustment of a retraction force applied to said soft tissue margins.

In another broad form the present invention comprises: an assembly allowing distraction of at least one vertebrae and retraction of soft tissue; the assembly comprising; means to apply a distraction load to said vertebrae via first and second distraction pins, a first retractor comprising a first side arm having a first end including a recess capable of engaging a first said pins anchored in a vertebrae, and a second end including connection means which releasably receives a first retractor arm via a mating profile; a second retractor having a second side arm having a first end including a recess capable of engaging a second of said pins and a second end including connection means which releasably receives a second retractor arm via a mating profile; wherein said respective connection means each allow rotatable adjustment of each said retractor arms for adjustment of a retraction force applied to said soft tissue margins.

In another broadest form the present invention comprises: a retraction assembly for retracting soft tissue the assembly comprising; a first set of jaws defining a recess for receiving therein a first pin attached to a first vertebrae and including an arm which receives and retains thereon a first retractor capable of rotation about said arm; a second set of jaws defining a recess for receiving therein a second pin attached to a second vertebrae and including an arm which receives thereon a second retractor capable of rotation about said arm.

In another broad form the present invention comprises: a retraction assembly comprising a first member including a first arm having a set of jaws defining a recess; a second arm extending from the first member; the second arm having means to receive and releasably retain a first retractor; a second member including a first arm having a set of jaws defining a recess; a second arm extending from the second member; the second arm on said second member having means to receive and releasably retain a second retractor; wherein, when the recess of said first member engages a first pin and the recess of said second member engages a second pin each said first and second retractors, retract wound margins in soft tissue; wherein each said retractors are rotationally adjustable relative to respective said second arms of said first and second members.

In another broad form the present invention comprises: a distraction and retraction assembly comprising; first and second anchor pins; sleeve members adapted to concentrically engage said pins for transmission of a distraction force on each pin; first and second retraction members; said first retraction member having a first arm having a set of jaws defining a recess which engages one said pins and a second arm extending from the first member; said second arm receiving and retaining a blade capable of retraction of soft tissue; said second retraction member including a first arm having a set of jaws defining a recess engaging a second one of said pins and a second arm extending from the second member; said second arm of said second retraction member comprising a blade capable of retraction of soft tissue; wherein, each said first and second arms engage via mating formations which allow lateral and rotational adjustment of each said first and second retractors.

According to a preferred embodiment each said set of jaws are disposed in a common plane and engage the pins anchored in vertebrae. According to one embodiment said jaws are disposed in an orientation which is normal to a longitudinal axis of said first and second arms. According to one embodiment, each said arms include spline formations which engage with corresponding formations on respective first and second retractors. According to a preferred embodiment the spline formations on each said arms provide a mating engagement which allows longitudinal and rotational adjustment of said arms.

According to a preferred embodiment each said blades include openings which receive and retain a tool adapted for adjustment of the orientation of said blades.

BRIEF DESCRIPTION OF THE DRAWINGS

FIG. 6 shows a perspective view of an assembly including an abbreviated retractor arm and joining member including a locating spline assembly according to one embodiment FIG. 7 shows the arrangement of FIG. 6 with retractor arm rotated to an alternative position disposed normally to the plane of the joining member.

FIG. 8 shows an exploded view of the assembly of FIG. 6.

FIG. 9 shows a retractor arm and joining member assembly according to an alternative embodiment.

FIG. 10 shows the retractor arm of FIG. 9 separated from the joining member

FIG. 11 shows an enlarged view of the joining member of FIG. 9.

FIG. 12 shows a retractor arm and joining member assembly according to an alternative embodiment.

FIG. 13 shows an enlarged view of the joining member of FIG. 12.

FIG. 14 shows a retractor arm and joining member assembly according to an alternative embodiment.

FIG. 15 shows an enlarged view of the joining member of FIG. 14.

DETAILED DESCRIPTION

Figure 1:
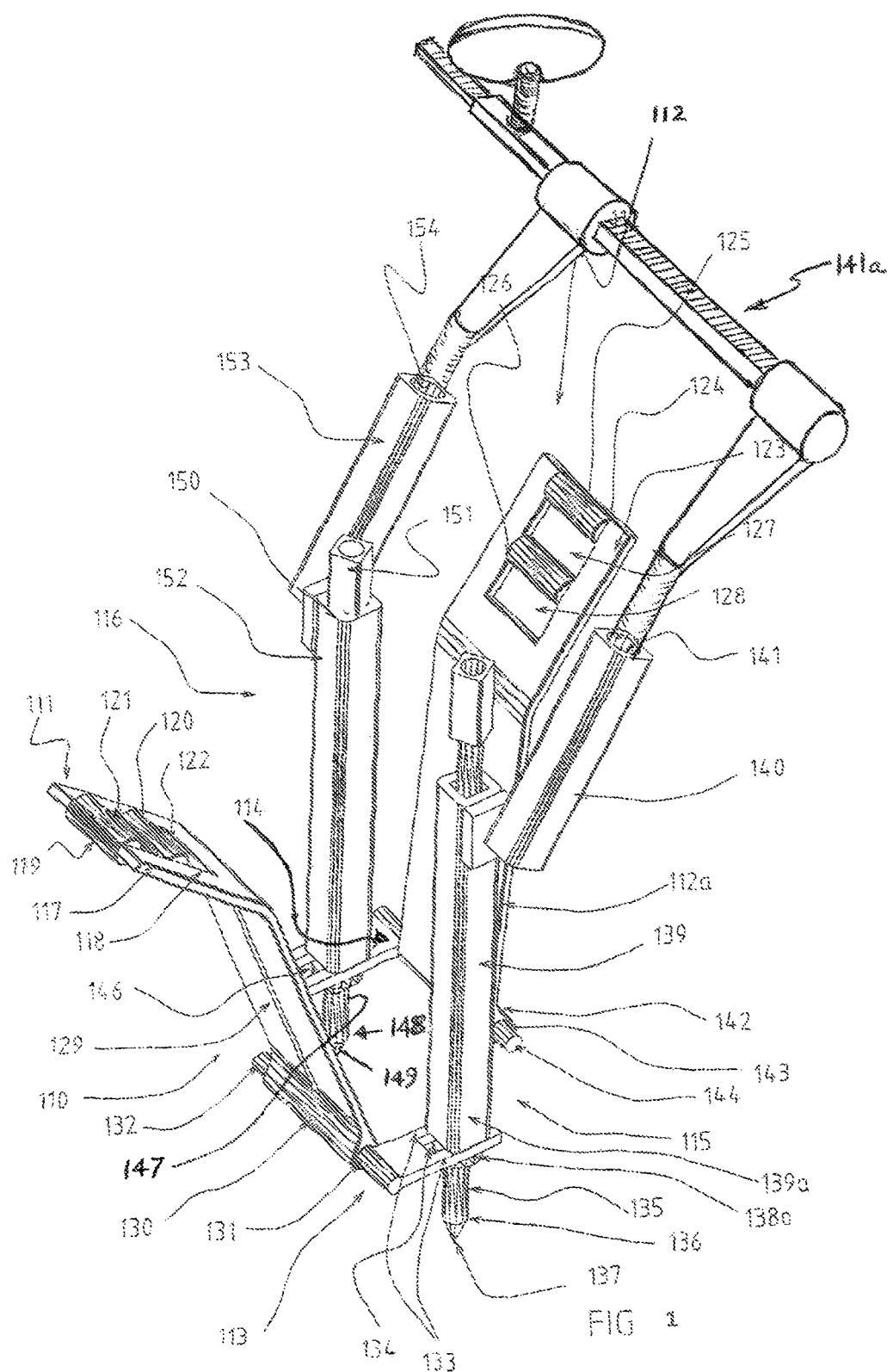
FIG. 1 shows a perspective view of a retractor assembly capable of concurrent distraction by co operating anchor pins according to a preferred embodiment.

The present invention will now be described in more detail according to a preferred embodiment but non limiting embodiment and with reference to the accompanying illustrations.

Typically according to one method, cervical distraction of vertebrae involves the use of anchor pins temporarily fixed to the vertebrae to be distracted. Generally two anchor pins are used one above and one below a disc or vertebral body of interest. Traditionally in a Caspar system these pins have only been used for distraction purposes via sliding tubes that fit axially over the pins and connect to an associated distraction mechanism. The role of the pin has been expanded to perform one or more of the following roles. The pin acts as x-ray marker to estimate a midline of a spine for cage or prosthetic disc replacement. The known and commonly used Caspar type distracter is then secured to the spine. Distracter tubes that each slide over respective pins and are secured to the pins via a screw applied at a threaded region. This however, does not have snug hex or square fit at a base of the pin but is round and transfers distraction forces along a length of a round pin. This does not provide optimal load transfer to the spinal vertebrae where distraction force is required but rather applies the load at a moment arm distant from the required load application site. The known technique for distraction force application applies a bending and shear force to the pins which must be transferred down the pin to its point of engagement with the vertebrae. A mechanical advantage during distraction is provided the closer the load is applied to the vertebrae due to a reduced moment arm and elimination of a bending moment on the pins so it is desirable to provide an assembly which meets this objective. In that case a shear force is applied at a base of pins to be distracted.

Throughout the specification a reference to a retractor arm may be taken to be synonymous with side arms, retractor blade and retraction member. A reference to blades will be taken to include a reference to retractors or retractor arms. To fully appreciate the various embodiments of the invention to be described below a summary of the bone fixation methodology and associated apparatuses and assemblies.

1. Bone Fixation
   Single Point Bone Fixation
   This is accomplished by screws or short spikes or a spike/screw combination. Spikes are useful where a line of pull is oblique to a line of insertion and where anatomy is unfavorable for screws. Multiples screws or spikes may be used. A portion of the screw or spike may engage an d link to other components. This portion is referred to as the anchor.

Anchor recess shapes which may be used (see figures) include the following non limiting embodiments:
   Mushroom (conical with enlarged point), Cone, dimple, cup for blade,
   Pedestal, Integral hinge and sidearm for connection to blade, Integral hinge allowing rotation in single plane, Integral small ball and socket with shaft for connection to blade.

2. Means of Rotation
   Anchor incorporates means of rotation anchor with built in shaft for blade attachment that allows rotation in 1 plane only.
   Anchor with built in ball and socket plus shaft for blade fixation that allows rotation in multiple planes.
   Link blade interface allows rotation either with integral or detachable hinge see FIG. 2, or as in. anterior cx system FIG. 1.
   Linking Components
   The various combinations of component include methods for securing components together, that may permit desired free rotation but may limit movement in other planes likely to produce loosening or fall out. It will be obvious to those skilled in the art that the mechanisms shown limiting unwanted motion are non limiting and that more simple versions of the following components with less stability are envisaged which prevents lift out once rotated. According to one embodiment there are links which lock rotation at the desired point such as the splines on retention members as shown in figure (FIGS. 1, 6, 7 and 8. Flathead with recess for locking pin. Once retractor blade rotates to certain angle e.g. 30 degrees recess is exposed allowing pin to be inserted from above down front of the blade. This pin is easily pulled out allowing free rotation of the blade but by insertion prevents blade returning until pin removed. Locking the retractor blade in this fashion means external handles for the blades or weights to pull the blade outwards are avoided. This reduces number of instruments around the operative field, frees or avoids totally the need for an assistant and facilitates x-rays.

According to one embodiment a retractor blade clicks into position from above which is an alternative to sliding components together but once together resist pull out directly unless slid out sideways.

FIG. 1 shows a perspective view of a retractor assembly capable of concurrent retraction and distraction by co operating anchor pins according to a preferred embodiment. Referring to FIG. 1 there is provided a retraction and distraction assembly 110 comprising retractor arms 111 and 112 terminating respectively in joining members 113 and 114 which engage anchor pin assemblies 115 and 116. Various shapes of retractor joining member/side arms are possible as required. Retractor arm 111 comprises a first free end portion 117 including a recess 118 and spanning therebetween bridge members 119 and 120. Bridge members 119 and 120 define spaces 121 and 122 which may attach to an operating tool not shown. The operating tool facilitates rotational movement of retractor arm 111. Retractor arm 112 comprises a first free end portion 123 including a recess 124 and spanning therebetween bridge members 125 and 126. Bridge members 125 and 126 define spaces 127 and 128 which may receive an operating tool not shown. As with arm 111, the operating tool facilitates rotational movement of retractor arm 112 such that arms 111 and 112 cooperate in maintaining retraction of opposing surgical wound margins. Arms 111 and 112 are in use disposed against opposing soft tissue wound margins during surgery to facilitate and maintain adjustable rotational retraction. Arm 111 further comprises blade region 129 which terminates in a formation 130 which defines a recess 131 which receives and retains therein joining arm 132 of joining member 113. This allows arm 111 to selectively rotate about joining arm 132. Joining member 113 also comprises a bifurcated portion 133 having two arms which define recess 134 which receives and retains anchorage assembly 115. Anchorage assembly 115 comprises an anchorage pin 135 having a leading end 136 terminating in a sharp point 137. Leading end 136 may have thread like screw or pin like to facilitate penetration in bone and a trailing end 138 providing a driving member 138a to facilitate bone penetration of point 137. Pin 135 is housed in guide sleeve 139 which compresses bifurcated portion 133. Joining member 113 locates between base 138a and end 139a of sleeve 139. Anchorage pin 135 which co operates with sleeve 139 has a leading end 136 terminating in a sharp point 137 to facilitate penetration in bone. Distal end 155 receives a driving member 156 to facilitate compression of sleeve 139a against bifurcated portion 133 securing joining member 113. Pin 135 is housed in guide sleeve 139 which engages bifurcated portion 133. Guide sleeve 139 has connected thereto an ancillary sleeve 140 which receives in recess 141 a tool (not shown) to facilitate distraction i.e. separation of anchorage assemblies 116 and 115 along an axis usually but not exclusively parallel to the axes of rotation of arms 111 and 112.

Arm 112 further comprises blade region 112a which terminates in a formation 142 which defines a recess 143 which receives and retains therein joining arm 144 of joining member 114. This allows arm 112 to selectively rotate about joining arm 144. Joining member 114 also comprises a bifurcated portion 145 having two arms which define recess 146 which receives and retains anchorage assembly 116. Anchorage assembly 116 comprises an anchorage pin 147 having a leading end 148 terminating in a sharp point 149 to facilitate penetration in bone and a trailing end 150 providing a driving member 151 to facilitate compression of sleeve 152 against bifurcated portion 145 securing joining member 114. Pin 147 is housed in guide sleeve 152 which engages bifurcated portion 145. Guide sleeve 152 has connected thereto an ancillary sleeve 153 which receives in recesses 154 and 141 a ratchet type distracting tool 141a, to facilitate distraction of anchorage assemblies 116 and 115 along an axis parallel to the axes of rotation of arms 111 and 112. The sleeves 152 and 139 engage onto square portions of respective pins. The bifurcated elements 133 and 145 also engage snugly around square portions of pins 135 and 147. This connection prevents independent rotation of elements. Combined rotation of all elements is prevented by joining two sleeves and pins together with an external distraction assembly. This distraction assembly (not shown) may join with the assembly as shown via recess 154 and 141 or may be integral as in existing Caspar systems.

With the above described assembly 110 a surgeon may selectively effect both distraction (of bone) and retraction (of soft tissues). The assembly allows distraction along an axis parallel to the axes of rotation of arms 111 and 112 and selective opposing rotational adjustments of arms 111 and 112 and if required removal of one or other of arms 111 and 112.

Figure 2:
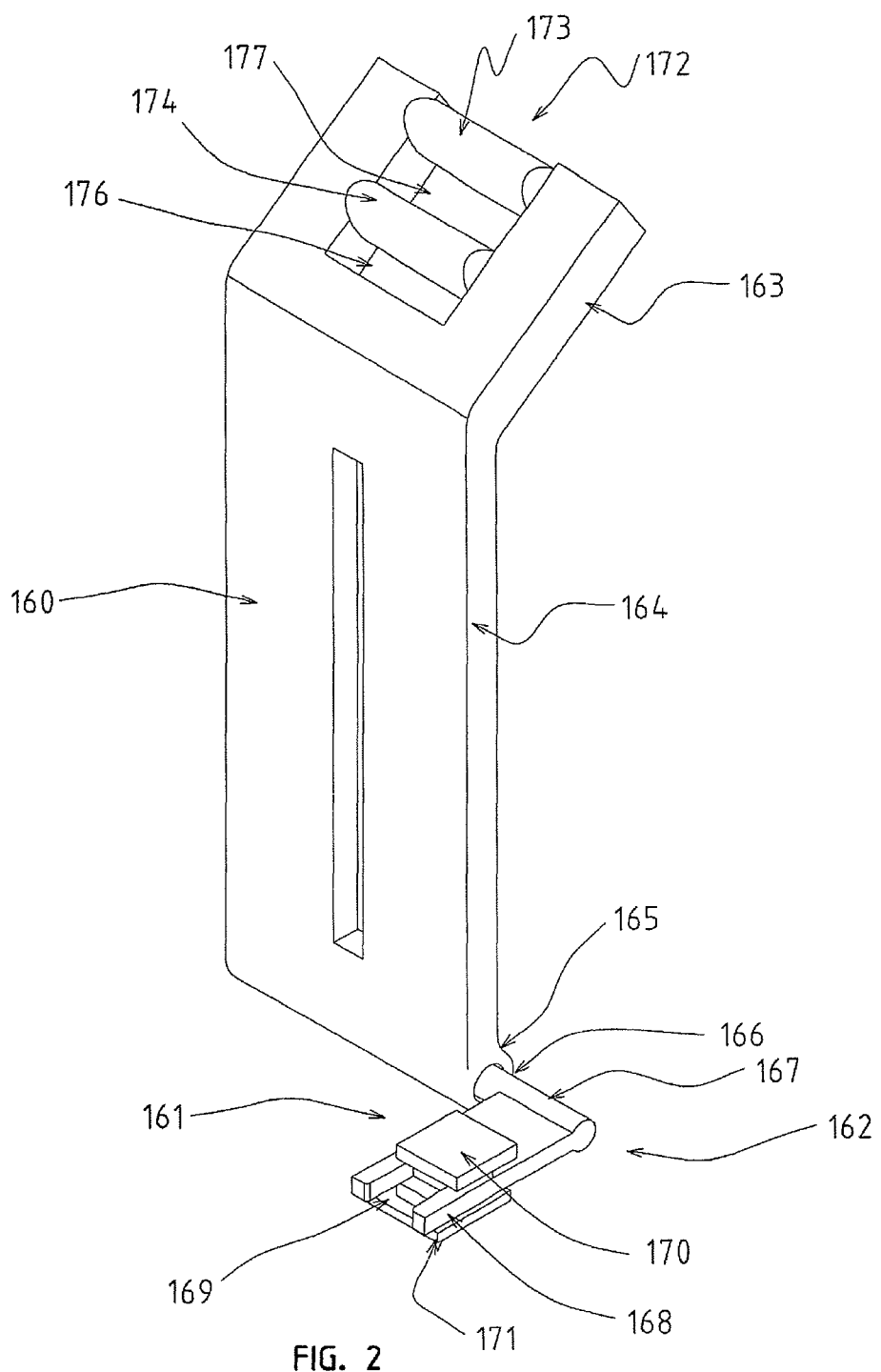
FIG. 2 shows a perspective view of a retractor assembly retraction arm anchored to an anchor pin by a joining member.

FIG. 2 shows a perspective view of a part retractor assembly showing retraction arm 160 anchored to an anchor pin 161 by a joining member 162 according to an alternative embodiment. Arm 160 comprises free end portion 163 and blade region 164 which terminates in a formation 165 which defines a recess 166 which receives and retains therein joining arm 167 of joining member 162. This allows retraction arm 160 to selectively rotate about joining arm 167. Joining member 162 also comprises a bifurcated portion 168 having two arms which define recess 169 which releasably receives and retains head 170 of anchorage pin 161 terminating in a sharp point 171 to facilitate penetration in bone. Free end portion 163 includes recess 172 which retains bridge members 173 and 174. Bridge members define openings 176 and 177 which receive an operating tool to facilitate both selective rotation of arm 160 and detachment from either joining member 162 or anchor 161.

Figure 3:
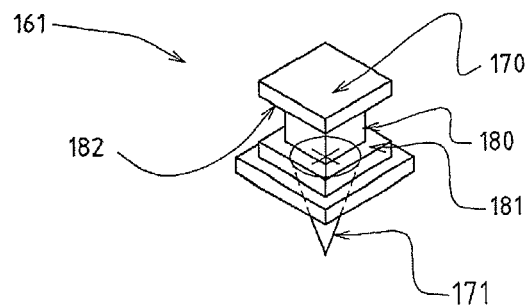
FIG. 3 shows an enlarged view of the retractor arm anchor pin of FIG. 2.

FIG. 3 shows an enlarged view of the retractor arm anchor pin 161 of FIG. 2 with corresponding numbering. Head 170 includes recess 180 which receives bifurcated portion 168 of joining member 162. Bifurcated portion 168 bears on shoulder 181 and locks against underside surface 182 of head 170. Shoulder 181 is optional and could be removed allowing bifurcated portion 168 of 162 to be positioned securely between 182 and base plate 170a.

Figure 4:
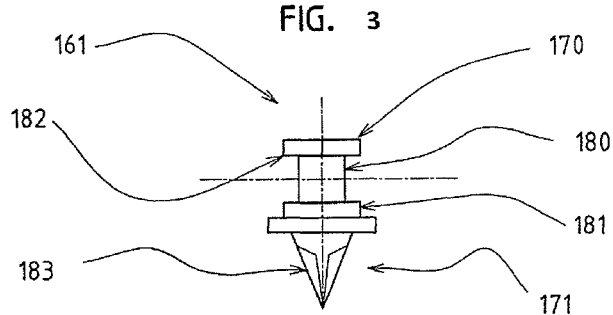
FIG. 4 shows an elevation view of the arm anchor pin of FIG. 3.
Figure 5:
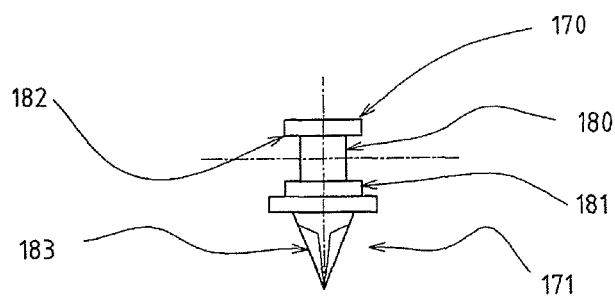
FIG. 5 shows an elevation view of the arm anchor pin of FIG. 3.

FIG. 4 shows an elevation view of the arm anchor pin 161 of FIG. 3 with corresponding numbering. Point 171 may further comprises formations 183 which facilitate bone penetration. FIG. 5 shows an elevation view of the arm anchor pin 161 of FIG. 6. This arrangement of blade secured to anchor pin 161 with mechanism permitting rotation has widespread application in but not limited to orthopaedic and spinal surgery and whenever bone fixation possible. Variations of such devices will be obvious to those skilled in the art.

Referring to FIG. 6 there is shown a perspective view of an assembly 260 including abbreviated retractor arm 261 and joining member 262 including locating spline assembly 263 according to one embodiment. FIG. 6 shows arm 261 at an oblique angle relative to a horizontal plane through joining member 262. FIG. 7 shows the arrangement of FIG. 6 with arm 261 rotated to an alternative position disposed normally to the plane of joining member 262. FIG. 8 shows an exploded view of the assembly 260 of FIG. 6. Joining member 262 includes a joining shaft 264 terminating in a free end 265 and having a knurled or bevelled surface. Member 262 terminates at its opposite end in a bifurcated member 266 which engages an anchor (not shown) similar to the arrangements previously described. Shaft 264 includes thereon a radial array of splines 267 extending from its circumferential surface 268. Arm 261 terminates in an enlarged region 269 having a wall 270 which defines a recess 271 adapted to axially receive shaft 264. Wall 270 has at one end 272 a radial array of elements 273 arranged to align with intermediate spaces between individual splines in spline array 267. This arrangement allows arm 261 to be selectively released from spline array 267 rotated to alternative positions such as shown in FIGS. 6 and 7. This allows a surgeon to selectively position the angle of repose of arm 261 held securely in position by splines 267. To reposition the angle of arm 261 this is axially released from splines 267, rotated and then reset. Splines provide a strong resistance to rotational loads applied against the arm 261 during use as a retractor.

In an alternative embodiment it will be appreciated that position of splines 267 on shaft 268 may be varied to opposite end 265 with a corresponding change of mating profile to other end of recess 271 and in a further embodiment blade could contain splines and the shaft the recesses. Opposite gender spline mating may also be employed.

The number of splines and teeth angles may be varied according to requirements. In an example of a method of use of the assembly, a surgeon may assemble the combined distracter and retractor assembly of FIG. 1 according to the following regime. Typically, the assembly may be employed in an anterior approach to the cervical spine. The first step which is based on a known technique involves insertion of pins in vertebrae to be distracted. Preferably there will be two pins 135 and 147 spaced apart which are distracted to allow access to a disc space in the case for instance where a disc is to be replaced. The distracter pins such as those described as in FIG. 1 are inserted into adjacent vertebrae. The surgeon takes a first retractor arm 111 or 112 whose configuration is selected to accommodate patient anatomy and allows it to directly or indirectly engage a first of said pins causing an associated rod and blade to lie generally parallel to a longitudinal axis of a spine. Arms 111 and 112 are mounted respectively on arms 132 and 144 of joining members 113 and 114. Sleeves 139 and 152 are positioned over respective pins 135 and 147. A retractor blade 111 or 112 such as that described with reference to FIG. 1 is attached if not previously done by sliding respective sleeves (130 and 142) on the blade along the pivot arm of a joining member 132, 144 until mating splines (or other mechanically equivalent engagement) engage. The orientation of the retractor blade is set according to a selected circumferential (rotational) engagement of the respective mating opposed splines. The assembly now formed and shown in FIG. 1 provides an ability to both distract vertebrae and retract soft tissue as required, the distraction occurring when a distraction force is applied through the sleeves or tubes 139 and 152 which axially engage the pins 136 and 147.

The degree of retraction is set by engaging the splines at a predetermined position so as to set the retractor arms 111 and 112 at an angle of repose which keeps soft tissue margins apart as required by the surgeon. If the aforesaid description relates to a right side distracter arm and retractor blade assembly there will be a corresponding left hand side arrangement which is preferably symmetrical about a transverse line through a disc space. If the aforesaid description relates to a left side distracter arm and retractor blade there will be a corresponding right hand side arrangement which is again symmetrical about a transverse line through the disc space. The distraction forces are applied at the base of the pins 136 and 147 to optimise mechanical advantage and to eliminate pin bending loads. This assembly described above allows variable distraction poses and movement without removal of retractors—side retractor arms and blades.

FIG. 9 shows a retractor arm and joining member assembly 200 according to an alternative embodiment. Assembly 200 comprises a retractor arm 201 and joining member 202 with the retractor arm 201 in a substantially vertical orientation. Arm 201 includes free end portion 203 and blade 204. End 203 includes bifurcation 205 defining recess 206. Recess 206 includes bridging members 207 and 208 defining recesses 209 and 210 which receive an operating tool (not shown) which in use facilitates arm rotation for retraction of soft tissues. Blade portion 204 terminates in an enlarged formation 211 defining a recess 212 having a partially cut away wall exposing the interior of recess 212. This cut away allows insertion and removal of members 202 and 222 plus rotation once centered. Recess 212 receives and retains joining member 202. FIG. 10 shows the retractor arm 201 of FIG. 9 separated from a joining member 202.

FIG. 11 shows an enlarged view of the joining member of FIG. 10. Joining member 202 is insertable in recess 212 via pivot arm 214. Pivot arm 214 has preferably intermediate its ends a bridge 215 which terminates in a loop 216 which engages an anchor pin (not shown). Arm 201 may then be rotated through about 30 degrees but it will be appreciated that the wall 217 (see FIG. 10) contains notch 217*a* that allows rotation of bridge 215 to occur limiting rotation as desired of recess 212 can be configured to achieve an alternative degree (more or less) of rotation.

FIG. 12 shows a retractor arm and joining member assembly 220 according to an alternative embodiment. Assembly 220 comprises a retractor arm 221 and joining member 222 with the retractor arm 221 abbreviated but in a substantially vertical orientation. Blade portion 223 terminates in an enlarged formation 224 defining a recess 225 having a partially cut away wall exposing the interior of recess 225.

FIG. 13 shows an enlarged view of the joining member of FIG. 12. Recess 225 receives and retains pivot retention arm 226 about which retractor arm 221 is free to rotate. Pivot arm 226 has preferably intermediate its ends a bridge 227 which terminates in an open saddle 228 which engages an anchor pin (not shown). Arm 221 may then be rotated as required about pivot arm 226.

FIG. 14 shows a retractor arm and joining member assembly 230 according to an alternative embodiment. Assembly 230 comprises a retractor arm 231 and joining member 232 with the retractor arm 231 abbreviated but in a substantially vertical orientation. Blade portion 233 terminates in an enlarged formation 234 defining a recess 235 having a partially cut away wall exposing the interior of recess 235. FIG. 15 shows an enlarged view of the joining member 232 of FIG. 14. Recess 235 receives and retains pivot arm 236 about which retractor arm 231 is free to rotate. Pivot arm 236 has preferably at one end a bridge 237 which terminates in an open saddle 238 which engages an anchor pin (not shown). Retractor arm 231 may then be rotated as required about pivot arm 236.

According to one aspect of the invention once the retractor blades are inserted they are fixed at or adjacent to a location where a tip of an end of the Retractor blade is required. This is usually deep in the wound and generally involves firm fixation to an adjacent bony surface via a screw, clamp or other gripping device that connects directly to the blade or via an intermediary linkage.

In most situations this connection with the fixation device will allow rotation of the blade about the point of fixation, either because the point of fixation itself can rotate. This fixation with rotation allows retractor blades to be left in situ throughout a procedure but allowing the surgeon to release the pressure and the retraction forces while working on another area thus reducing the tissue trauma but without having to remove the retractor blade or reposition the retractor blade. Releasing self retaining retractors leads to repeated tissue trauma every time these are reinserted and/or reopened. This system would therefore reduce tissue trauma and save time. It would also mean that the retractor once appropriately inserted can be secured insitu and not become loose or dislodged and require repositioning. The fixation device described in the cervical assembly utilises a pin with a screw thread into the bone and is first embodiment of this principal.

This components described have multiple applications for the purpose of retraction of tissues. Such assemblies could also act as components in distraction devices alone or be combined with function as base for rotating retractors as illustrated in FIG. 1.

It will be appreciated by those skilled in the art that the utilisation of this principal could be used in numerous other applications adapting to the different anatomy and retraction requirements throughout the spine, musculoskeletal system or wherever bony fixation can be utilised, e.g. the head. It will be further recognised by persons skilled in the art that numerous variations and modifications may be made to the invention without departing from the overall spirit and scope of the invention broadly described herein. Such modifications would allow adaptation of key concepts (which is that retractor blades are fixed at or close to critical point of retraction and may rotate) to provide additional retraction devices for use in anterior or posterior spinal surgery throughout length of spine or in orthopaedics or other surgical disciplines where bony fixation is available.

The invention claimed is:

1. An assembly capable of retraction of soft tissue and distraction of bone during surgical procedures, the assembly comprising:
   an anchorage which anchors the assembly to said bone;
   at least one retractor arm having a first free end and a second end, the second end including a formation which allows the at least one retractor arm to each be detachably retained by a retaining member, the formation allowing said at least one retractor arm to be capable of movement at least rotationally about an axis at said second end, which is transverse to a longitudinal axis through said at least one retractor arm;
   the anchorage including two anchorage pins each having anchorage pin formations to enable anchorage of the anchorage pins to said bone; and
   a frame assembly including each of said retaining member which respectively receive said second end of each said retractor arms to facilitate said rotation;
   wherein the frame assembly is generally U shaped such that first and second retaining arms are parallel and includes at least one opening each of which are configured to receive one said anchorage element enabling fixation of the frame assembly to bone;
   two said retaining members on opposite sides of the frame assembly each configured to receive one of the retractor arms;
   a first bridge joining the retaining members; each retractor arm configured to engage a corresponding formation on the second end of the retaining members, allowing the retractor arms to rotate about the retaining members and slide therealong; each of the said retaining members have a first end attached to said first bridge and a second free end;
   wherein the formation on each said retractor arm is a recess which at least partially receives therein at least part of one said retaining members, allowing the retractor arm to undergo said rotation and sliding therealong;
   wherein the frame assembly has a second bridge including openings to allow engagement with said free ends of said retaining members; and wherein the first and second bridges each include an opening to allow penetration of a first anchorage pin through the first bridge and a second anchorage pin through the secondary bridge for screw fixation of the assembly to bone.

2. An assembly according to claim 1, wherein the retractor arms rotate in a plane normal to a longitudinal axis of said retention members.

3. An assembly according to claim 2, wherein said retaining arms include a gripping region which cooperates with the recess in said retractor arms and which facilitates selective rotation of the retractor arms.

4. An assembly according to claim 3, wherein the retractor arms are incrementally rotationally adjustable about said retention members to increase or decrease soft tissue retraction capacity.

5. An assembly according to claim 4, wherein said anchorage elements allow distraction of bone segments when inserted.

6. An assembly according to claim 5, wherein the assembly is capable of simultaneous distraction of bone by relative movement of the first and secondary bridges and retraction of soft tissue.

7. An assembly according to claim 6, wherein said anchorage pins are each retained by a sleeve which cooperate to assist distraction.

8. An assembly according to claim 7, wherein fixation of said pins allows said retractor arms to rotate about respective retention members.

9. An assembly according to claim 8, wherein each bone anchor pin includes a leading end screw thread which fixes the pin to said bone.

10. A retraction and distraction assembly for use in soft tissue retraction and bone distraction, the assembly comprising:
    a frame assembly including two retention members and first and second bridge members each having an opening which accommodates an anchorage for engaging bone to anchor the retraction and distraction assembly;
    the first bridge member joining the retention members, wherein each of said retention members has a first end attached to said first bridge and a second free end; the retention members each receiving and retaining thereon at least one retractor arm having a first free end and a second end, the second end including a formation which allows the retractor arm to be detachably retained by said retention members enabling said retractor arms to rotate about said retention members and slide therealong.

11. An assembly according to claim 10, wherein the second bridge member includes openings which engage and cooperate with said retention members.

12. A frame assembly according to claim 11, wherein two retention members receive respective opposing retractor arms.

13. An assembly according to claim 12, wherein each retention member engages the formation on the second end of the retractor arms, allowing each of the retractor arms to rotate about respective retention members and slide therealong.

14. An assembly according to claim 13, wherein the frame assembly is shaped such that the first and second retention members are parallel and disposed normally to the bridge members.

15. An assembly for combined retraction of wound margins of soft tissue and distraction of vertebrae during spinal surgery, the assembly comprising:
    a pair of distraction pins configured to be anchored in said vertebrae and which transfer an applied distraction force via sleeves;
    said sleeves concentrically engaging said pins;
    a first retention member having a first end including a recess capable of engaging one of said pins and a second end including a connection which receives a first retractor arm via a cooperating mating profile; and
    a second retention member having a first end including a recess capable of engaging the other of said pins and a second end including a connection which releasably receives a second retractor arm via a mating profile, wherein said first and second retractor arms are capable of selective rotation about said retention members to retract soft tissue margins during surgery.

16. An assembly according to claim 15, wherein the retention members include spline formations providing a mating engagement which allows longitudinal and rotational adjustment of said retraction arms about and along said retention members.

\* \* \* \* \*